(12) United States Patent
McInerney et al.

(10) Patent No.: US 7,614,303 B2
(45) Date of Patent: Nov. 10, 2009

(54) DEVICE FOR MEASURING BULK STRESS VIA INSONIFICATION AND METHOD OF USE THEREFOR

(75) Inventors: Michael K. McInerney, Champaign, IL (US); Sean W. Morefield, Champaign, IL (US); Vincent F. Hock, Jr., Mahomet, IL (US); Victor H. Kelly, West Chester, PA (US); John M. Carlyle, Yardley, PA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 338 days.

(21) Appl. No.: 11/727,600

(22) Filed: Mar. 27, 2007

(65) Prior Publication Data

US 2008/0236285 A1 Oct. 2, 2008

(51) Int. Cl.
*G01N 29/024* (2006.01)
(52) U.S. Cl. .............................. 73/597; 73/598; 73/602; 73/761
(58) Field of Classification Search .................... 73/597, 73/598, 602, 760, 761
See application file for complete search history.

(56) References Cited

U.S. PATENT DOCUMENTS

| | | | | |
|---|---|---|---|---|
| 4,602,511 A | * | 7/1986 | Holt | 73/581 |
| 5,969,260 A | * | 10/1999 | Belk et al. | 73/773 |
| 6,354,152 B1 | * | 3/2002 | Herlik | 73/597 |
| 7,317,314 B2 | * | 1/2008 | Zimmermann et al. | 324/209 |
| 7,360,435 B2 | * | 4/2008 | Nassar et al. | 73/761 |
| 7,441,462 B2 | * | 10/2008 | Kibblewhite | 73/761 |
| 2009/0031811 A1 | * | 2/2009 | Georgeson et al. | 73/588 |
| 2009/0038401 A1 | * | 2/2009 | Kibblewhite | 73/761 |

OTHER PUBLICATIONS

Landa, M. and J. Plesek; Ultrasonic Techniques for Non-Destructive Evaluation of Internal Stresses; Institute of Thermomechanics ASCR, Dolejskova 5, 18200, Praha 8, Czech Rep., (Oct. 15-21, 2000).

* cited by examiner

*Primary Examiner*—J M Saint Surin
(74) *Attorney, Agent, or Firm*—Earl H. Baugher, Jr.

(57) ABSTRACT

A configuration for use with a processor that incorporates a suite of agents in a "flat" hardware architecture and superimposes thereon a self-forming, self-healing, hierarchical architecture implemented in software. Embodiments may be employed in various applications, such as maintaining network integrity. In one embodiment a building security monitoring network provides for automated network agents to each be capable of communication with any other automated agents on a network at network startup. Shortly after network initialization, the software architecture is superimposed on the flat hardware architecture, re-arranging communication links to provide an efficient hierarchy of control and substituting working agents for compromised agents as necessary in the network. All of this is done in a "live" network, not requiring shutdown, or even reduced operation to accomplish. This "dual" architecture (hierarchical software and flat hardware) provides excellent reliability in those "layered" network applications requiring near total reliability, such as security surveillance.

20 Claims, 2 Drawing Sheets

DEVICE FOR MEASURING BULK STRESS VIA INSONIFICATION AND METHOD OF USE THEREFOR

STATEMENT OF GOVERNMENT INTEREST

Under paragraph 1(a) of Executive Order 10096, the conditions under which this invention was made entitle the Government of the United States, as represented by the Secretary of the Army, to the entire right, title and interest therein of any patent granted thereon by the United States. This patent and related ones are available for licensing. Contact Bea Shahin at 217 373-7234.

BACKGROUND

Select embodiments of the present invention may be used to measure stress in tensioned members of critical structures. This measure of stress is also referred to as "bulk tension." In many cases access to these members is limited, e.g., steel reinforcing members buried in concrete. Critical structures include dams, bridges, elevated highways, nuclear containment domes, parking garages, piers, tunnels, and the like.

Acoustic waves are nondestructive and are capable of traveling long distances in engineered structures. Further they can be used to "interrogate" a structure to determine its integrity. Acoustic "interrogation" signals may be employed for purposes of determining bulk properties and to detect defects. Bulk properties, such as tension, are determined by acoustic signals interacting macroscopically with material, whereas, defects are identified by acoustic signals interacting microscopically with material. These dual purposes are achieved by carefully shaping transmitted acoustic signals and using tailored signal processing techniques on the reflected signals. Acoustic interrogation can identify both bulk properties and defects, quantifying results quickly, i.e., in "near real-time" although custom processing may extend display of results by one or two minutes.

There are two common types of ultrasonic waves, longitudinal and shear. Other types of ultrasonic waves exist, such as surface waves and plate waves. For a longitudinal wave, also termed compressional wave, particles vibrate in a direction that is the same as the propagation direction. For a shear wave, particles vibrate in a direction that is perpendicular to the propagation direction. Shear wave velocities, $V_s$, are typically about half of longitudinal wave velocities, $V_l$. Shear waves do not exist in some media, such as water and air, although solid media support shear waves.

Landa and Plesek employed shear waves in a technique that is both reasonably sensitive and linear. Landa, M. and J. Plesek, *Ultrasonic Techniques for Non-Destructive Evaluation of Internal Stresses*, Institute of Thermomechanics ASCR, Dolejskova 5, 18200, Praha8, Czech Republic, October, 2000. Their technique is limited to using shear waves that are polarized in two directions, parallel to the principal stress axis and transverse to the principal stress axis. These shear waves propagate in the remaining direction across the principle stress axis. Propagation parallel to the principal stress axis is preferable.

A select embodiment of the present invention now enables inspectors to quickly and easily make a quantitative determination of damage or degradation of post-tensioned members or objects. Prior to the present invention, two methods were commonly available for this purpose. The first is a "hammer test" that produces a first acoustic tone when the object is under zero or low tension and a second noticeably different tone when under designed (moderate or high) tension. Obviously, the hammer test yields a purely qualitative result. The second method involves the use of a jack, such as a hydraulic jack and is termed a "jacking test." It often requires attaining "reasonable" access to members that otherwise have limited access. Jacking is both laborious and expensive when used to determine the condition of post-tensioned members in the field. While the jacking test is quantitative, it cannot be used in many situations because of restricted access considerations, expense, or both.

U.S. Pat. No. 5,154,081, Means and Method for Ultrasonic Measurement of Material Properties, to Thompson et al., Oct. 13, 1992 employs two electromagnetic acoustic sensors arranged on a single side of an object to be measured. Stress measurements are limited to those available near a surface of ferromagnetic objects having a large accessible surface. No measurements are made throughout the bulk of the object.

U.S. Pat. No. 5,289,387, Method for Measuring Stress, to Higo, et al., Feb. 22, 1994, uses a variety of sensor types and placements on metal, polycarbonates or acryl resin objects to measure bulk stress. The '387 patent measures attenuation of ultrasound to determine stress. Since attenuation is an indirect measurement, i.e., not related to fundamental ultrasonic properties, this method is limited to measuring very well characterized objects, such as standard items in a production line. For example, it cannot be used successfully on unknown parts picked at random.

U.S. Pat. No. 6,477,473, Ultrasonic Stress Measurement Using the Critically Refracted Longitudinal (LCR) Ultrasonic Technique, to Bray, Nov. 5, 2002, uses two sensors in a specific arrangement placed on a single side of an object. The sensors measure a reflection angle to determine longitudinal wave speed and hence stress. This device is limited to objects with accessible large surfaces since it measures the velocity of a longitudinal wave only.

None of these patents provide a device or method for determining tension in a randomly picked object that may have only a limited surface available for access, such as a reinforcing member embedded in concrete. Embodiments of the present invention differ from existing ultrasonic instruments, such as the StressTel®, BoltMike® and the like, that measure tension in bolts. These instruments measure elongation of a bolt while it is being torqued. They are "tension (bolting) control systems" that depend upon measuring changes in length between the un-loaded and the loaded (stressed) conditions of a particular fastening device, such as a bolt. Thus, unlike an embodiment of the present invention, they cannot measure stress in a fastener, such as a bolt or screw, that was tightened prior to use of the instrument.

From first principles of ultrasonic theory a relationship for calculating stress (tension) in a part using only the shear and longitudinal velocities may be derived as follows:

$$\sigma = \frac{(V_l^2 - 2V_s^2)}{2(V_l^2 - V_s^2)} \tag{1}$$

where $V_l$ is the longitudinal wave velocity and $V_s$ is the shear wave velocity and $\sigma$ is the bulk stress (tension) along the principal stress axis of the structure to be measured. However, Eqn. (1) has been relegated to theory and not adapted for use because heretofore both shear and longitudinal velocities were unable to be measured simultaneously and accurately. Select embodiments of the present invention address this limitation by employing Eqn. (1) in the design of a robust, portable, efficient and relatively inexpensive package. Further, embodiments of the present invention do not require using shear waves that are polarized in two directions, i.e., parallel to the principal stress axis and transverse to the principal stress axis, to propagate in the remaining direction across the principle stress axis. Instead, applying Eqn. (1) allows calculation of bulk stress (bulk tension) by using acoustic energy, preferably ultrasound, propagated parallel to the principal stress axis.

Select embodiments of the present invention are able to address a wider range of situations than is possible using prior techniques. An embodiment of the present invention is useful for accurately determining the bulk stress inside an object that may offer limited access in its permanent installation, such as a reinforcing member buried in concrete, a post-tensioned element used in dams or bridges, and the like. An accurate measure of the bulk stress in a reinforcing member is critical for determining the structural integrity of damaged buildings; in making "repair or replace" decisions on existing structures; in determining the extent of deterioration of infrastructure; in researching degradation of materials, and in like applications. An embodiment of the present invention is also useful for accurately determining the strength of undamaged walls, e.g., resistance to penetration.

Select embodiments of the present invention may be provided in a portable package. Further, select embodiments of the present invention are able to limit the imposition of the acoustic signal to small areas, essentially points, for improved resolution.

DETAILED DESCRIPTION

In select embodiments of the present invention, a method is provided for obtaining a measure of stress in an object. The method comprises: establishing the length of the object along a first axis; providing one or more sensors, each sensor having one each first and second elements, and first and second connectors mounted on a proximal end, the first connector associated with the first element and the second connector associated with the second element, such that the first element facilitates communicating one or more acoustic signals, preferably ultrasonic, in the form of a shear wave and the second element facilitates communicating one or more acoustic signals, preferably ultrasonic, in the form of a longitudinal wave; coating at least part of the distal end with a shear gel (e.g., "shear honey"); bringing the distal end of the sensor into contact with the object; producing first and second acoustic signals, preferably ultrasonic; applying the first signal to the first connector to transmit the first signal via the first element; receiving a first reflection, i.e., a reflection of the first signal from the distal end of the first axis in the form of a shear wave; and establishing the elapsed time from initial transmission of the first signals at the sensor to receipt of the first reflections at the sensor; processing the elapsed time with the established length of the first axis to yield a first estimate, $V_s$, of the velocity of the first signals in the object; applying the second signal to the second connector to transmit the second signal via the second element in the form of a longitudinal wave; receiving a second reflection, i.e., a reflection of the second signal from the distal end of the first axis; establishing the elapsed time from initial transmission of the second signals at the sensor to receipt of the second reflections at the sensor; processing the elapsed time with the established length of the axis to yield a second estimate, $V_l$, of the velocity of the second signals in the object; and employing one value each of $V_l$ and $V_s$ in an algorithm, thus deriving a measure of stress.

In select embodiments of the present invention, the sensor is provided in a housing, the connectors are provided through an external surface of the proximal end of the housing, and the distal end of the housing is suitable to transmit an acoustic signal. In select embodiments of the present invention, the housing is provided as a cylinder.

Example I

Figure 1:
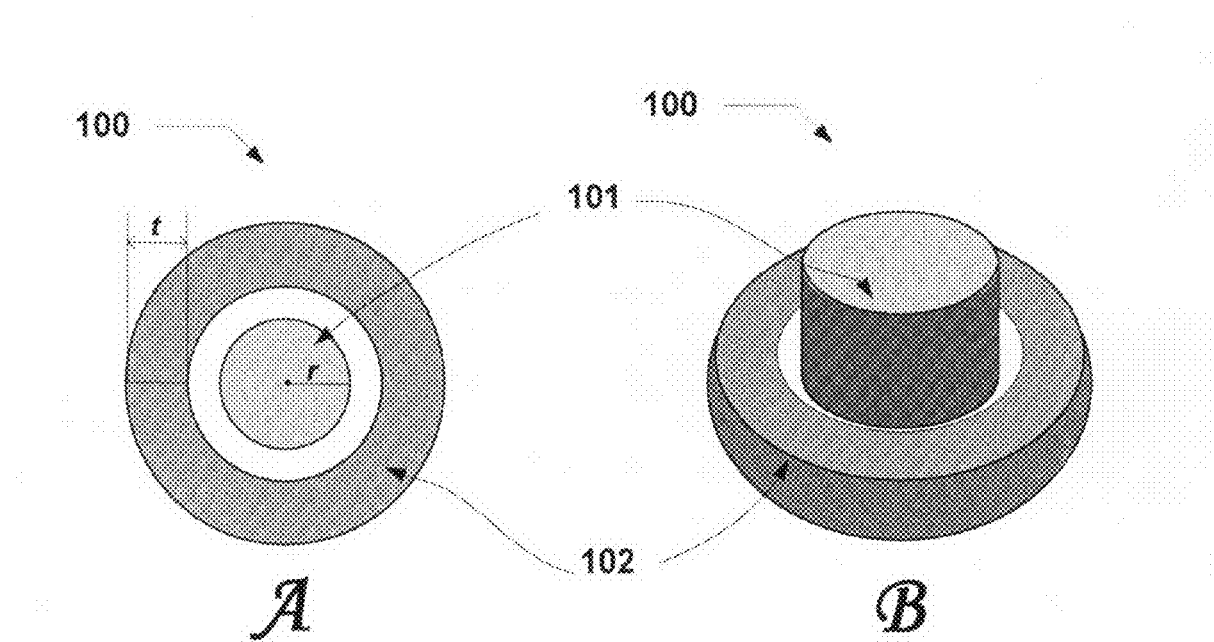
FIG. 1 provides top and side views of the two elements incorporated in the sensor of an embodiment of the present invention.

Refer to FIG. 1. FIG. 1 at A provides a top view of a sensor 100 that may be used in select embodiments of the present invention. FIG. 1 at B provides a perspective view of the sensor 100 at A with the center element 101 partially removed. In select embodiments of the present invention, the method provides the first element 101 as a solid cylinder concentric with a longitudinal axis of the sensor 100 and the second element 102 as a hollow cylinder of wall thickness, t, arranged concentrically about the first element 101, such that t is approximately equal to the radius, r, of the first element 101.

In select embodiments of the present invention, the method provides an acoustic signal as an ultrasonic signal. In select embodiments of the present invention, the method provides an algorithm employing Eqn. (1), such that a measure of stress along a first axis (most likely the longitudinal axis) of the object is obtained.

In select embodiments of the present invention, the method establishes a first axis of the object as the principal stress axis of the object.

Figure 2:
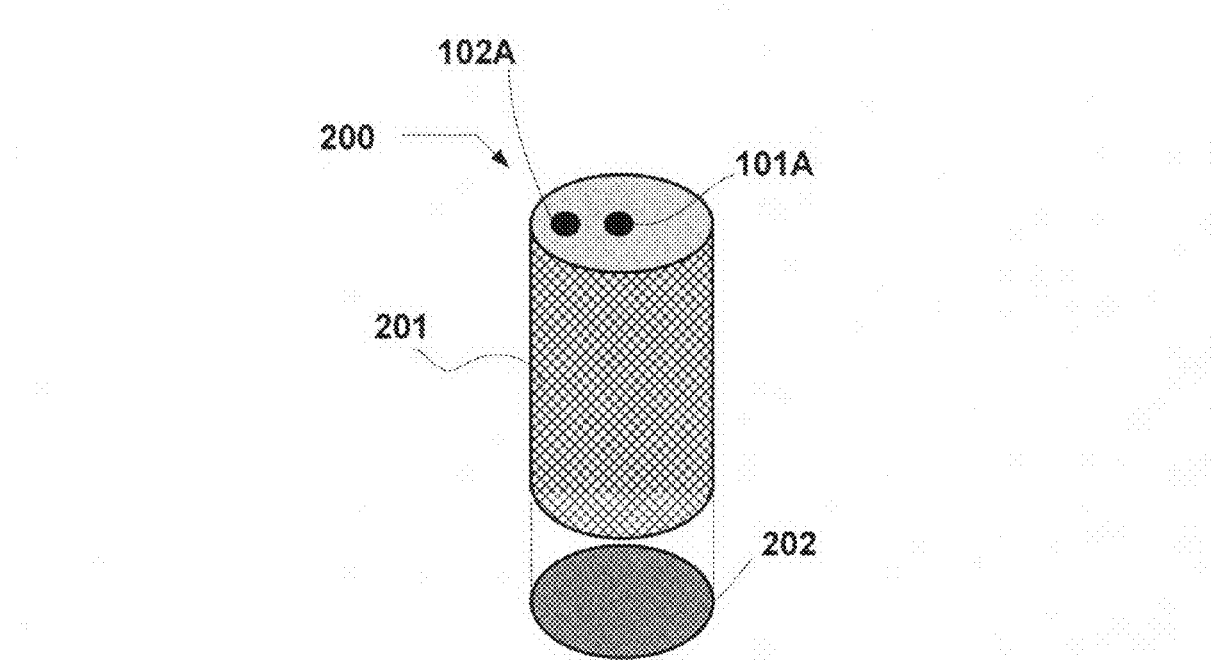
FIG. 2 illustrates an external view of salient features of a sensor package that may be used with an embodiment of the present invention.

Refer to FIG. 2, a perspective view showing a packaged sensor 201 and the proximal end containing the connectors 101A, 102A for the sensor 100 of FIG. 1, the distal end being defined during operation of the system as that end contacting the object (not shown separately) being tested. In select embodiments of the present invention, a device for measuring bulk stress along a first axis of an object, comprises: a housing 201 containing a sensor 100 having first 101 and second 102 elements and corresponding first 102A and second 102A connectors, the first 102A and second 102A connectors positioned on a proximal end of the housing 201, the first connector 101A affixed to the first element 101 and the second connector 102A affixed to the second element 102, such that the first element 101 facilitates communicating acoustic signals represented by a shear wave, and the second element 102 facilitates communicating acoustic signals represented by a longitudinal wave; one or more sources (shown in FIG. 3 as part of 300) of acoustic signals, preferably ultrasonic, such that the sources produce first and second signals, preferably acoustic, the parameters of each signal being similar; one or more processors (shown in FIG. 3 as part of 300) for processing the signals and reflections thereof from the distal end of the first axis of the object; and an algorithm loaded on a CPU 305, the algorithm employing the measured shear and longitudinal wave velocities, $V_s$ and $V_l$, of the signals from the first 101 and second 102 elements, respectively, such that processing the algorithm provides an accurate quantitative measure of bulk stress in near real time.

In select embodiments of the present invention, a sensor 100 is incorporated in a housing 201 such that the connectors 101A, 102A are provided through an external surface of the proximal end of the housing 201 and the distal end of the housing 201 is at least partially coated with shear gel (e.g., shear honey) and suitable to transmit acoustic signals from the object to a processor. In select embodiments of the present invention, the housing 201 is a hollow configuration, such as a cylinder, with a wear plate 202 (shown lifted from the sensor housing 201 in FIG. 2) at its distal end to permit the sensor 100 to contact the object being tested. The elements 101, 102 are epoxied (to facilitate the conduction of the acoustic waves, and particularly the shear wave) between the two metallized ends of the elements 101, 102 to the metallized face of the wear plate 202, such as a silicon dioxide wear plate, which contacts the object via shear gel.

Refer to FIGS. 1 and 2. In select embodiments of the present invention, the first element 101 is a solid cylinder concentric with a longitudinal axis of the sensor 100 and the second element 102 is a hollow cylinder of wall thickness, t, arranged concentrically about the first element, such that t is approximately equal to the radius, r, of the first element 101.

Figure 3:
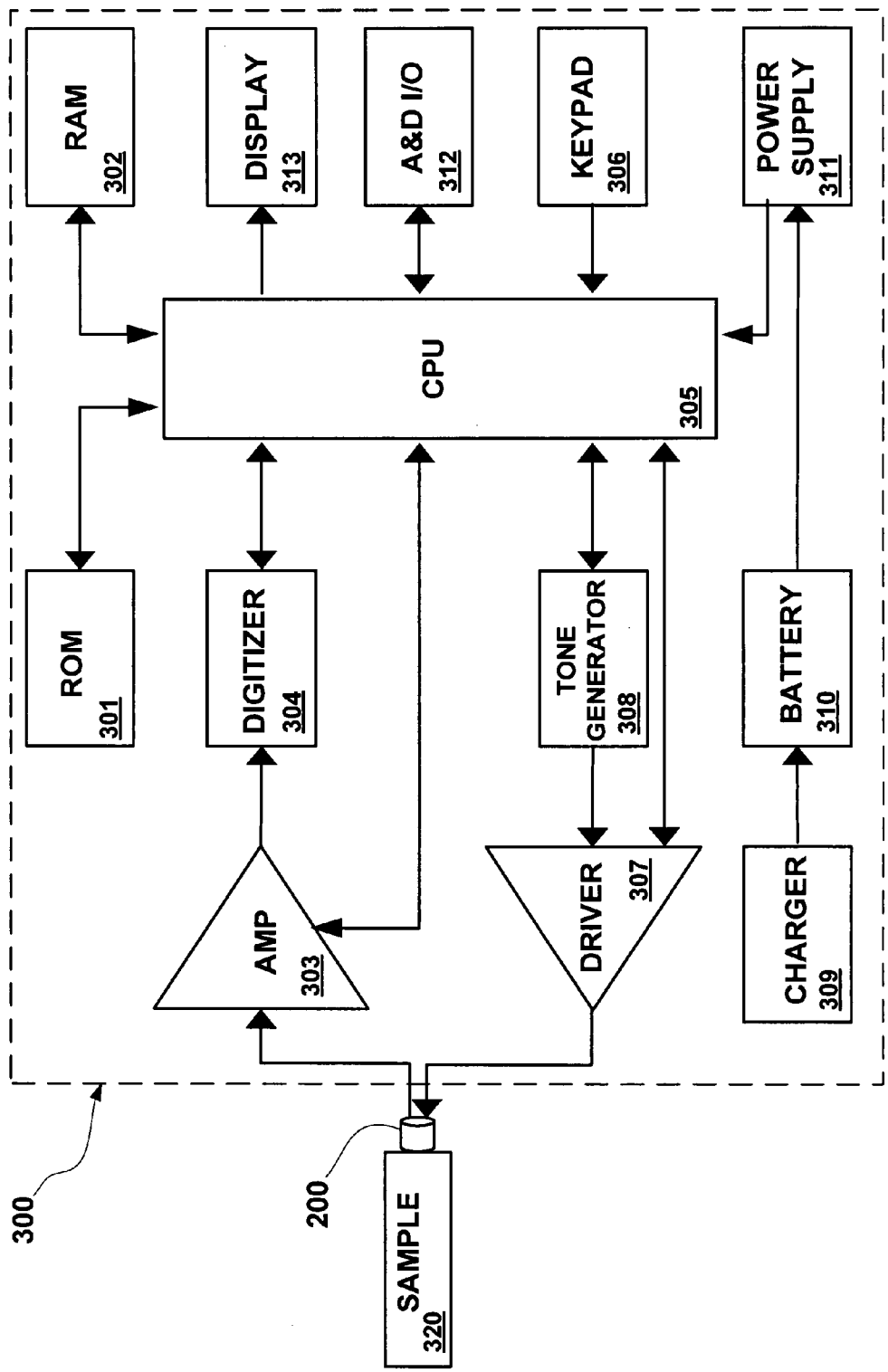
FIG. 3 is a block diagram of system components incorporated in an embodiment of the present invention employed in measuring stress.

In select embodiments of the present invention, the source is one or more ultrasonic signal sources, such as a tone generator (represented at 308 in FIG. 3). In select embodiments of the present invention, the algorithm employs Eqn. (1) to convert measures of shear and longitudinal wave velocity in the object to a measure of bulk stress along the first axis of the object. In select embodiments of the present invention, the first axis of the object (represented as Sample 320 in FIG. 3) is established as the principal stress axis of the object, the length of the first axis being established a priori.

Refer to FIG. 3, a block diagram showing the relationships among various components of select embodiments of the present invention. In select embodiments of the present invention, the sources further comprise one or more drivers (represented as 307 in FIG. 3) connected to each of the sources.

Refer to FIG. 3. In select embodiments of the present invention, the processor comprises: one or more amplifiers (represented as 303) communicating with the packaged sensor 200, the amplifier 303 amplifying reflected signals; one or more digitizers (represented as 304) communicating with the amplifiers 303; one or more computers communicating with the digitizer 304, the computer comprising: one or more central processing units (CPU) (represented as 305); one or more Read Only Memories (ROM) (represented as 301) communicating with the CPU 305; one or more Random Access Memories (RAM) 302 communicating with the CPU 305; one or more displays (represented as 313) communicating with the CPU 305; one or more keypads 306 communicating with the CPU 305; one or more Analog and Digital Input/Output (A&D I/O) devices (represented as 312) communicating with the CPU 305; and one or more power supplies (represented as 311) communicating with the CPU 305.

Refer to FIG. 3. In select embodiments of the present invention, the device further comprises one or more batteries (represented as 310) communicating with the power supply 311. In select embodiments of the present invention, the device further comprises one or more battery chargers (represented as 309) suitable to be placed in communication with one or more batteries 310.

Refer to FIG. 1. In select embodiments of the present invention, an acoustic sensor 100 for facilitating obtaining a measure of bulk stress along a first axis of an object, comprises: one each first 101 and second 102 elements and one each first 101A and second 102A connectors, the first 101A and second 102A connectors positioned on the proximal end of the sensor 100, the first connector 101A connected to the first element 101 and the second connector 102A connected to the second element 102, such that the first element 101 facilitates communicating an acoustic signal in the form of a shear wave and the second element 102 facilitates communicating an acoustic signal in the form of a longitudinal wave.

Refer to FIG. 2. In select embodiments of the present invention, the sensor 100 is incorporated in a housing 201 such that the connectors 101A, 102A are provided through an external surface of a proximal end of the housing 201 and the distal end of the housing 201 is at least partially coated with shear gel and suitable to transmit acoustic signals with minimal loss at the interface of the sensor 100 and the object. In select embodiments of the present invention, the sensor housing 201 is a cylinder.

Refer to FIG. 1. In select embodiments of the present invention, the first element 101 of the sensor 100 is a solid cylinder concentric with a longitudinal axis of the sensor 100 and the second element 102 is a hollow cylinder of wall thickness, t, arranged concentrically about the first element, such that t is approximately equal to the radius, r, of the first element 101.

Refer to FIG. 1, illustrating an embodiment of the present invention, a dual wave sensor 100, incorporating two elements 101, 102 that produce different modes of ultrasonic waves. The center element 101 of the sensor 100 is uniquely fashioned so that it produces shear waves that vibrate perpendicular to the sound propagation axis instead of longitudinal waves that vibrate parallel to the sound propagation axis. The outer annular element 102 of the sensor 100 produces longitudinal waves as would be expected from a conventional acoustic device. Individual sensors 100 are sized to the wavelength of the acoustic energy to be used with it and the intended object to be measured.

Example II

One example of material to use in a sensor 100 of the present invention is piezoelectric material. To use piezoelectric material to generate ultrasound, connect wires on either side of the piezoelectric material and connect these wires in parallel to a high voltage pulse generator (not shown separately) as well as to an overload protected high gain amplifier (not shown separately) with output connected to an oscilloscope (not shown separately). Impress the piezoelectric material on the object to be tested. When the high voltage pulse (signal) activates the piezoelectric material the sensor 100 changes shape, creating a "stress" pulse (signal) that is, in turn, impressed upon the object to be tested. If the acoustic impedance is small enough at the interface between the sensor 100 and the object, the signal propagates from the sensor 100 into the object, e.g., a piece of rebar under load. Use of a shear gel (shear honey) often insures a good acoustical contact, i.e., a sufficiently small impedance. A properly applied signal will propagate to the end of the object and reflect back to the sensor 100. The reflected signal hits the boundary between the object and the sensor 100 and some of the reflected signal is transmitted to the sensor 100. At this point the reflection distorts the shape of the piezoelectric material, producing a small voltage in the wires connecting the sensor to the high gain amplifier. The amplifier raises the voltage level to a point where the signal may be discerned on the oscilloscope display. From this round trip signal, the transit time of the signal in the material is determined. In this example, a spike corresponding to the high voltage pulse that starts the process appears at the left hand edge of the oscilloscope display. This is followed some time later by a smaller spike corresponding to the reflection that is closer to the right hand edge of the display. The time between the spikes corresponds to the roundtrip travel time of the impressed signal.

Eqn. (1) permits calculation of bulk stress by measuring the velocity of acoustic longitudinal and shear waves only, i.e., by using ultrasonic waves propagating parallel to the principal stress axis of the structure being tested.

Example III

Refer to FIG. 3, a block diagram of an ultrasonic instrument 300 that may be used in an embodiment of the present invention. In select embodiments of the present invention, a suitable ultrasonic instrument is a digitally based unit, Model DFX544, manufactured by Dakota Ultrasonics®. It offers precision, controllable ultrasonic pulse generation and accurate timing features. Any acoustic instrument, preferably ultrasonic, that provides the features of: generating a suitable tone; transmitting the tone to a sensor made in accordance with operating parameters of the present invention, receiving a reflected signal; and processing the transmitted and received signals for suitable display and analysis is satisfactory.

Refer to FIG. 3. A Central Processing Unit (CPU) 305 associated with Read Only Memory (ROM) 301 and Random Access Memory (RAM) 302, all of which may be on one or more circuit boards within the instrument 300, may be used to control the process of taking bulk stress measurements in accordance with an embodiment of the present invention. Associated with the CPU 305 are a display 313, such as a CRT, an LCD, and the like; one or more Analog and Digital input/output devices (A&D I/O) 312; a keypad 306, such as a QWERTY keyboard or the like; and a power supply 311 such as may be used in either a desktop or laptop personal computer of conventional design or the like. The CPU 305 and any of the above peripherals may be incorporated in a single instrument, such as those marketed by Dakota Ultrasonics®. Further, the signal processing may be done entirely with analog devices so that an A/D converter is not required.

An embodiment of the present invention may be provided as a portable, stand-alone instrument with the addition of one or more batteries 310. Further, a battery charger 309 may be incorporated in select embodiments of the present invention, capable of operating from sources that are either AC (such as commercial power) or DC (such as a 12 V automotive battery), or both.

A tone generator 308 provides an acoustic signal, preferably an ultrasonic signal, to a driver 307 for transmission to a sensor package 200 fabricated in accordance with an embodiment of the present invention. Once a signal is transmitted via a particular one of the two elements 101, 102, into the sample 320 to be measured, the reflected analog acoustic signal is captured and amplified by amplifier 303 and passed to a digitizer 304 to be digitized prior to processing in the CPU 305. For each measurement, a tone (acoustic signal) is generated and transmitted separately over each sensor element 101, 102 to yield a pair of "roundtrip" transmission times for the two separate tones (signals) used with each measurement. Preferably the two separate tones are sent using similar parameters, e.g., frequency, amplitude, modulation, and the like. The transmission times are processed in the CPU 305 using an algorithm employing Eqn. (1) and a measurement of the bulk stress in the sample is derived.

In select embodiments of the present invention, a sensor package 200 is mounted on a sample 320 that has had shear gel applied thereto to serve as an acoustical couplant. Note that conventional ultrasonic coupling substances, such as water, oil or grease and the like, are not suitable because they do not transmit the shear component of acoustic waves. The ultrasonic instrument 300 is then connected to the shear wave element 101 of the sensor package 200 at the appropriate connector 101A, and a measurement is made of the roundtrip time of the ultrasonic pulse to and from the distal surface of the sample 320. This process is then repeated, using the longitudinal wave element 102 and the appropriate connector 102A. The measured longitudinal and shear travel times are each divided by twice the length of the sample 320, and the resultant velocities, $V_l$ and $V_s$, are used in Eqn. (1) to calculate the bulk stress in the sample 320. Multiple tests may be run and an average of the results used as necessary to assure consistency of data.

The sensor 200 generates both shear waves and longitudinal waves from the same housing 201, eliminating problems associated with accurate shear and longitudinal sound velocity measurement taken conventionally in two separate mountings of the sensor. That is, both a shear wave and a longitudinal wave may be propagated from the exact same position of the sensor as mounted on the object to be measured. With conventional sensors, the sensor would need to be un-mounted to get a second reading for the wave not propagated the first time. Further, multiple mountings and readings may be taken with an embodiment of the present invention with little concern for errors from multiple mountings since the algorithm uses the difference between shear and longitudinal velocities. In select embodiments of the present invention, the distance over which the velocity of both shear and longitudinal waves are measured is the same as the ultrasonic coupling and propagation path. With three sources of variance eliminated accurate bulk stress measurements are made. Note that an embodiment of the present invention is not limited to any specific type of material. Further, an embodiment of the present invention is applied at a single point, i.e., it does not require access to a large surface area of the object. Note that an embodiment of the present invention provides an accurate quantitative measure of true bulk stress, not just simple surface stress.

Example IV with Test Results

A test load was applied to a steel bolt, 4.275 in. long with a shank diameter of 0.625 in. and a minimum thread area cross section of 0.85 square inches. The load was applied manually using a hydraulic jack and a hollow plunger cylinder with an effective area of 2.76 square inches. The applied hydraulic pressure was read from an analog gauge. The resulting load on the bolt and the resulting bolt tension were calculated from the applied hydraulic pressure, using the cylinder effective area for the first quantity and the bolt minimum cross sectional area for the second quantity. The settings used for this test are given in Table 1.

TABLE 1

| Test settings for tensioning a 4.275 in. steel bolt | | |
|---|---|---|
|  | LONGITUDINAL | SHEAR |
| FREQUENCY (MHz) | 2.25 | 2.25 |
| AMPLITUDE (Volts) | 200 | 200 |
| PULSE WIDTH (nsec) | 280 | 280 |
| PRF (Hz) | 35 | 35 |
| RECEIVER GAIN (dB) | 25 | 25 |
| DAMPING (Ohms) | 400 | 400 |
| DETECTION (RF) | FULL | FULL |

Ultrasonic velocities were determined by using an embodiment of the present invention, a prototype ultrasonic bulk stress measurement sensor coupled to a Dakota Ultrasonics DFX-544 instrument to time the longitudinal and shear wave transits. Dividing the known bolt length by transit times yielded the required shear and longitudinal velocities, $V_s$ and $V_l$ for use in Eqn (1). The calculated bolt tension was found by using Eqn (1), referencing to zero, and multiplying by an appropriate experimental constant, 10293483, which is about ⅓ of Young's modulus of steel. Results are displayed in Table 2.

TABLE 2

Test results from tensioning a 4.275 in. steel bolt.

| Bolt Tension (psi) | Velocity: Longitudinal (in/s) | Velocity: Shear (in/s) | Calculated Bolt Tension (psi) | Experimental Error |
|---|---|---|---|---|
| 0 | 233809 | 127421 | 0 | 0% |
| 1625 | 233754 | 127405 | 658 | −59% |
| 3249 | 233645 | 127405 | 3553 | 9% |
| 4874 | 233590 | 127389 | 4212 | −14% |
| 6498 | 233481 | 127372 | 6320 | −3% |
| 8123 | 233372 | 127340 | 7637 | −6% |
| 9747 | 233263 | 127324 | 9747 | 0% |

From this laboratory test on a small object, the experimental error is greatest at small loads. The error was introduced in the measurement of the time for the shear wave to traverse the small object. If the bolt tension calculated from this erroneous time was instead calculated from the "no load" shear velocity value, the experimental error would be −11%. Looking at this another way, if a tensioned member expected to have a nominal loading exhibits tension values that are unexpectedly low then one might conclude that the tensioned member is broken or weakened and needs further investigation.

Example V

If one were to use an embodiment of the present invention for testing supporting infrastructure of a large concrete monolith, such as the Henry dam, the settings may be as those presented in Table 3. Thus, one can see that the settings are tailored to the application to which an embodiment of the present invention is put, one change being the provision of a much stronger signal for larger objects.

TABLE 3

Test settings for tensioning steel rods of approximately 40 ft. in length.

|  | LONGITUDINAL | SHEAR |
|---|---|---|
| FREQUENCY (MHz) | 2.25 | 2.25 |
| AMPLITUDE (Volts) | 400 | 400 |
| PULSE WIDTH (nsec) | 250 | 250 |
| PRF (Hz) | 35 | 35 |
| RECEIVER GAIN (dB) | 92 | 108 |
| DAMPING (Ohms) | 400 | 400 |
| DETECTION (RF) | FULL | FULL |

In addition to determining the bulk stress of reinforcing material in critical structures, an embodiment of the present invention may be used to determine the strength of concrete structure, e.g., resistance to penetration. Select embodiments of the present invention may be used to assess the strength of structure, such as that damaged by terrorist action or during battle. Many engineered structures, such as bridges, dams, parking garages, and the like require periodic inspection and maintenance to identify and correct any deteriorating reinforcement members. Select embodiments of the present invention can assist owners in making "repair or replace" decisions, while simultaneously increasing the safety of the general public.

Select embodiments of the present invention aid researchers with real-time measurements of strength degradation during materials testing. Measurements of stress and strain are common in laboratories, however, conventional methods take stress measurements globally over the specimen. An embodiment of the present invention measures bulk stress in a small column-shaped section of interest. This offers early determination of the effects of degradation. That is, select embodiments of the present invention provide the ability to see strength degradation in pre-specified zones rather than just macroscopically.

It is therefore to be understood that within the scope of the appended claims, the invention may be practiced otherwise than as described. Accordingly, all such modifications are intended to be included within the scope of this invention as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

The abstract is provided to comply with the rules requiring an abstract, which will allow a searcher to quickly ascertain the subject matter of the technical disclosure of any patent issued from this disclosure. 37 CFR § 1.72(b). Any advantages and benefits described may not apply to all embodiments of the invention.

We claim:

1. A method for obtaining a measure of bulk stress in an object, comprising:

establishing the length of said object along a first axis of interest, said first axis having a proximal and distal end;

providing at least one sensor package having a proximal and distal end, said sensor package having at least one each first and second elements, at least one each first and second connectors positioned on said proximal end, said first connector in operable communication with said first element and said second connector in operable communication with said second element, wherein said first element facilitates communicating at least one acoustic signal in the form of a shear wave, and wherein said second element facilitates communicating at least one acoustic signal in the form of a longitudinal wave;

coating at least part of said distal end of said sensor with shear gel;

bringing said distal end of said sensor package into contact with said object;

producing internally at least first and second electromagnetic signals for conversion to first and second acoustic signals;

applying said first electromagnetic signal to said first connector to transmit said first acoustic signal out of said first element;

receiving at least one first reflection of said first acoustic signal from said distal end of said first axis; and establishing the elapsed time from initial transmission of said first acoustic signals at said sensor to receipt of said first reflections at said sensor;

processing said elapsed time with said established length of said object to yield at least one first estimate, $V_s$, of the velocity of said first acoustic signals in said object;

applying said second electromagnetic signal to said second connector to transmit said second acoustic signal via said second element;

receiving at least one second reflection of said second acoustic signal from said distal end of said first axis;

establishing the elapsed time from initial transmission of said second acoustic signals at said sensor to receipt of said second reflections at said sensor;

processing said elapsed time with said established length of said object to yield at least one second estimate, $V_l$, of the velocity of said second acoustic signals in said object; and employing one value each of $V_l$ and $V_s$ in an algorithm, deriving said measure of bulk stress.

2. The method of claim 1 providing said sensor package in a housing having a proximal and distal end, said connectors provided through an external surface of said proximal end of said housing and said distal end of said housing configured such that said sensors may contact said object and transmit said acoustic signals into said object.

3. The method of claim 2 providing said acoustic signal as an ultrasonic signal.

4. The method of claim 1 providing said first element as a solid cylinder concentric with a longitudinal axis of said sensor package and providing said second element as a hollow cylinder of wall thickness, t, arranged concentrically about said first element, wherein t is approximately equal to the radius, r, of said first element.

5. The method of claim 1 providing said algorithm employing the relationship:

$$\sigma = \frac{(V_l^2 - 2V_s^2)}{2(V_l^2 - V_s^2)}$$

wherein σ is said measure of bulk stress along said first axis of said object.

6. The method of claim 1 establishing said first axis of said object as the principal stress axis of said object.

7. A device for obtaining a measure of bulk stress along a first axis of an object, comprising:

at least one sensor package having a proximal and a distal end, said sensor package having at least one each first and second elements and at least one each first and second connectors, said first and second connectors positioned on said proximal end, said first connector in operable communication with said first element and said second connector in operable communication with said second element, wherein said first element facilitates communicating at least one acoustic signal in the form of a shear wave, and wherein said second element facilitates communicating at least one acoustic signal in the form of a longitudinal wave;

shear gel;

wherein said shear gel is coated on at least part of said distal end of said sensor or said object at point of contact of said sensor package with said object;

at least one source of acoustic signals, wherein said source produces at least first and second acoustic signals;

at least one processor for processing said signals and reflections thereof from said distal end of said first axis of said object; and at least one algorithm, said algorithm employing one value each of the velocities, $V_s$ and $V_l$, of said signals from said first and second elements, respectively, wherein processing said algorithm provides said measure of bulk stress.

8. The device of claim 7 in which said sensor package is incorporated in a housing having a proximal and distal end, wherein said connectors are provided through an external surface of said proximal end of said housing, and wherein said distal end of said housing is configured to transmit said acoustic signals when facilitated by a coating of said shear gel.

9. The device of claim 8 in which said housing is a cylinder having said elements epoxied to a wear plate to facilitate the conduction of acoustic waves and particularly said shear wave between said elements and said wear plate that contacts said object via said shear gel.

10. The device of claim 7 in which said first element is a solid cylinder concentric with a longitudinal axis of said sensor package and said second element is a hollow cylinder of wall thickness, t, arranged concentrically about said first element, wherein t is approximately equal to the radius, r, of said first element.

11. The device of claim 7 in which said algorithm employs the relationship:

$$\sigma = \frac{(V_l^2 - 2V_s^2)}{2(V_l^2 - V_s^2)}$$

wherein σ is said measure of bulk stress along said first axis of said object.

12. The device of claim 7 in which said source further comprises at least one driver in operable communication with said source.

13. The device of claim 7 in which said processor further comprises:

at least one amplifier in operable communication with said sensor for amplifying said reflections;

at least one digitizer in operable communication with said amplifier;

at least one central processing unit (CPU) in operable communication with said digitizer;

at least one Read Only Memory (ROM) in operable communication with said CPU;

at least one Random Access Memory (RAM) in operable communication with said CPU;

at least one display in operable communication with said CPU;

at least one keypad in operable communication with said CPU;

at least one Analog and Digital Input/Output (A&D I/O) device in operable communication with said CPU; and at least one power supply in operable communication with said CPU.

14. The device of claim 13 further comprising at least one battery in operable communication with said power supply.

15. The device of claim 14 further comprising at least one battery charger to be placed in operable communication with at least one said battery.

16. An acoustic sensor package having a proximal and a distal end, said sensor package facilitating obtaining a measure of bulk stress along a first axis of an object, comprising:

at least one each first and second elements and at least one each first and second connectors, said first and second connectors positioned on said proximal end, said first connector in operable communication with said first element and said second connector in operable communication with said second element, wherein said first element facilitates communicating at least one acoustic signal in the form of a shear wave, and wherein said second element facilitates communicating at least one acoustic signal in the form of a longitudinal wave; and a housing, having a proximal and distal end, incorporating said elements and said connectors, wherein said connectors are provided through an external surface of said proximal end of said housing, and wherein said distal end of said housing is configured to transmit said acoustic signals, and wherein said distal end of said housing or said portion of said object contacting said sensor is at least partially coated with shear gel.

17. The sensor of claim 16 further comprising a wear plate at said distal end and in which said housing is a cylinder having said elements epoxied to said wear plate to facilitate the conduction of acoustic waves and particularly said shear wave between said elements and said wear plate that contacts said object via said shear gel.

18. The sensor of claim 16 in which said first element is a solid cylinder concentric with a longitudinal axis of said sensor and said second element is a hollow cylinder of wall thickness, t, arranged concentrically about said first element, wherein t is approximately equal to the radius, r, of said first element.

19. A device for measuring bulk stress along a first axis of an object, comprising:

first means for detecting acoustic energy, said first means having a proximal and a distal end, said first means having at least one each first and second elements and at least one each first and second connectors, said first and second connectors positioned on said proximal end, said first connector in operable communication with said first element and said second connector in operable communication with said second element, wherein said first element facilitates communicating at least one acoustic signal in the form of a shear wave, and wherein said second element facilitates communicating at least one acoustic signal in the form of a longitudinal wave; shear gel;

wherein said shear gel is coated on at least part of said distal end of said first means or on a portion of said object in contact with said device;

at least one means for generating acoustic signals, wherein said means for generating acoustic signals produces at least first and second acoustic signals;

at least one means for processing said acoustic signals and reflections thereof from said distal end of said object along said first axis; and at least one algorithm, said algorithm employing one value each of the velocities, $V_s$ and $V_l$, of said signals from said first and second elements, respectively, wherein processing said algorithm provides said measure of bulk stress.

20. The device of claim 19 in which said acoustic signals are ultrasonic signals.

* * * * *

UNITED STATES PATENT AND TRADEMARK OFFICE
CERTIFICATE OF CORRECTION

PATENT NO. : 7,614,303 B2
APPLICATION NO. : 11/727600
DATED : November 10, 2009
INVENTOR(S) : Michael K. McInerney et al.

It is certified that error appears in the above-identified patent and that said Letters Patent is hereby corrected as shown below:

Title page, Item (57)

Replace the Abstract printed on the patent with the Abstract filed with the application:

A device and method to nondestructively measure bulk stress in a member by employing an acoustic source, preferably an ultrasonic source, a processor, and a uniquely configured acoustic sensor package. The sensor package is configured to transmit both a longitudinal wave signal and a shear wave signal into the member. The processor is configured to capture reflections of the two impressed signals along a principal stress axis of the member and calculate the roundtrip time of the two signals. Knowing the length of the member along a principal stress axis, from the roundtrip times of the two signals, two velocities are calculated. By employing an equation that calculates bulk stress as a function of these shear and longitudinal wave velocities, a measure of bulk stress is calculated via the processor. The device measures bulk stress of a member that offers limited access in its permanent installation, such as dam reinforcements.

Signed and Sealed this

Thirtieth Day of November, 2010

David J. Kappos
*Director of the United States Patent and Trademark Office*